United States Patent
Manda et al.

(10) Patent No.: US 7,632,234 B2
(45) Date of Patent: Dec. 15, 2009

(54) IMPLANTABLE BIOSENSOR DEVICES FOR MONITORING CARDIAC MARKER MOLECULES

(75) Inventors: Ven Manda, Stillwater, MN (US); Tommy D. Bennett, Shoreview, MN (US); Zhongping Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 568 days.

(21) Appl. No.: 10/652,837

(22) Filed: Aug. 29, 2003

(65) Prior Publication Data

US 2005/0049472 A1    Mar. 3, 2005

(51) Int. Cl.
 *A61B 5/02* (2006.01)
(52) U.S. Cl. .............. 600/508; 607/9; 607/17; 607/22
(58) Field of Classification Search ........................ None
 See application file for complete search history.

(56) References Cited

U.S. PATENT DOCUMENTS

| | | | |
|---|---|---|---|
| 5,024,222 A * | 6/1991 | Thacker ................... | 607/22 |
| 5,040,533 A * | 8/1991 | Fearnot ................... | 607/22 |
| 5,334,222 A * | 8/1994 | Salo et al. ................ | 607/17 |
| 6,124,430 A | 9/2000 | Mischak et al. | |
| 6,169,925 B1 | 1/2001 | Villaseca et al. | |
| 6,461,828 B1 | 10/2002 | Stanton et al. | |
| 6,671,527 B2 * | 12/2003 | Petersson et al. ........... | 600/316 |
| 6,965,791 B1 * | 11/2005 | Hitchcock et al. .......... | 600/345 |
| 7,016,714 B2 * | 3/2006 | Colvin, Jr. ................ | 600/316 |
| 7,074,194 B2 * | 7/2006 | Crosby et al. .............. | 600/508 |
| 7,127,290 B2 * | 10/2006 | Girouard et al. ............ | 607/17 |
| 2001/0021821 A1 * | 9/2001 | Wang et al. ................ | 604/110 |
| 2002/0117659 A1 | 8/2002 | Lieber et al. ............... | 257/14 |
| 2002/0120186 A1 | 8/2002 | Keimel ..................... | 600/365 |
| 2003/0022235 A1 | 1/2003 | Dahlen et al. .............. | 435/7.1 |
| 2003/0055461 A1 | 3/2003 | Girouard et al. ............ | 607/17 |
| 2003/0114735 A1 * | 6/2003 | Silver et al. ............... | 600/300 |
| 2003/0204212 A1 * | 10/2003 | Burnes et al. .............. | 607/17 |
| 2003/0220552 A1 * | 11/2003 | Reghabi et al. ............. | 600/365 |

(Continued)

FOREIGN PATENT DOCUMENTS

WO    WO 02/083913 A1    10/2002

(Continued)

OTHER PUBLICATIONS

Troughton et al., Treatment of Heart Failure Guided by Plasma Aminoterminal Brain Matruretic Peptide (N-BNP) Concentrations, The Lancet, vol. 355, (2000) pp. 1126-1130.

(Continued)

*Primary Examiner*—Patricia Mallar
*Assistant Examiner*—Karen E Toth
(74) *Attorney, Agent, or Firm*—Stephen W. Bauer

(57) ABSTRACT

An implantable biosensor system is disclosed for determining levels of cardiac markers in a patient to aid in the diagnosis, determination of the severity and management of cardiovascular diseases. The sensor includes nanowire sensor elements having a biological recognition element attached to a nanowire transducer that specifically binds to the cardiac marker being measured. Each of the sensor elements is associated with a protective member that prevents the sensor element from interacting with the surrounding environment. At a selected time, the protective member may be disabled, thereby allowing the sensor element to begin sensing signals within a living body.

23 Claims, 8 Drawing Sheets

U.S. PATENT DOCUMENTS

| | | | |
|---|---|---|---|
| 2004/0082841 A1* | 4/2004 | Furnary et al. | 600/325 |
| 2004/0147966 A1* | 7/2004 | Ding et al. | 607/9 |
| 2004/0243010 A1* | 12/2004 | Zoghbi et al. | 600/508 |
| 2004/0254419 A1* | 12/2004 | Wang et al. | 600/8 |
| 2005/0020895 A1* | 1/2005 | Christopherson et al. | 600/345 |
| 2005/0096516 A1* | 5/2005 | Soykan et al. | 600/317 |

FOREIGN PATENT DOCUMENTS

WO     WO 03/016901 A1     2/2003

OTHER PUBLICATIONS

Bettencourt, et al., Evaluation of Brain Natriuretic Peptide in the Diagnosis of Heart Failure, Cardiology 2000:93-19-25.

Boomsma et al., Plasma A- and B-type Natriuretic Peptides: Physiology, Methodology and Clinical Use, Cardiovascular Research 51 (2001) 442-449.

Cheng et al., A Rapid Bedside Test for B-Type Peptide Predicts Treatment Outcomes . . . , Jour. of American College of Cardiology (2001), pp. 386-391.

Cui et al., Nanowire Nanosensors for Highly Sensitive and Selective Detection of Biological and Chemical Species, Science, vol. 293, (2001), pp. 1289-1292.

Maisel, Alan, B-Type Natriuretic Peptide Levels: A Potential Novel "White Count" for Congestive Heart Failure, Journal of Cardiac Failure, vol. 7, No. 2, (2001), pp. 183-193.

Talwar et al., Towards a Blood Test for Heart Failure: The Potential Use of Circulating Natriuretic Peptides, 2000 Blackwell Science Ltd Bar J Clin. Pharmacol. 50, 15-20.

Tamura et al., Prognostic Impact of Plasma Brain Natriuretic Peptide For Cardiac Events in Edlerly Patients . . . , Clinical Section, Gerontology 2001; 47:46-51.

Dao, et al., Wtility of B-Type Natriuretic Peptide in the Diagnosis of Congestive Heart Failure . . . , Journ. of American College of Cardiology, vol. 37, No. 2 (2001).

* cited by examiner ns in a patient, and particularly, to biosensors suitable for implantation to provide in vivo detection and/or monitoring of one or more cardiac markers.

IMPLANTABLE BIOSENSOR DEVICES FOR MONITORING CARDIAC MARKER MOLECULES

FIELD OF THE INVENTION

The present invention relates to sensors for detecting, measuring and/or monitoring levels of physiological analytes in a patient, and particularly, to biosensors suitable for implantation to provide in vivo detection and/or monitoring of one or more cardiac markers.

BACKGROUND OF THE INVENTION

Heart disease, including myocardial infarction, is a leading cause of death and impaired activity in human beings, particularly in the western world. Ischemic heart disease is the major form of heart failure. A common symptom of cardiac ischemia is chest pain that may lead to heart attack (acute myocardial infarction or AMI) and sudden death.

Myocardial ischemic disorders occur when blood flow in the heart is restricted (ischemia) and/or when the oxygen supply to heart muscle is compromised hypoxia) and the heart's demand for oxygen is not met. Ischemia and hypoxia can be transient and reversible, but can also lead to a heart attack. During such an attack, cardiac tissue is damaged and the heart cells become permeabilized, releasing a portion of their contents to the surrounding environment, including cardiac enzymes and other biochemical markers. These cellular markers, such as creatine kinase (CK), lactic acid dehydrogenase (LDH) and creatine kinase-MB (CKMB) and troponin (I and T) and myoglobin mass levels become detectable in the blood of the patient. The use of these markers and new forms of treatment has increased the survival rate of patients having a heart attack. This factor combined with the increased life expectancy has led to an increase in the prevalence of congestive heart failure (CHF).

CHF causes significant morbidity and mortality, and the health care expenditure for this disease is substantial. The need exists for better diagnostic and prognostic methods for this disease. Recently, assays for B-type natriuretic peptide (BNP) which is secreted by the ventricles in response to ventricular expansion and pressure overload resulting in an elevation of the plasma concentration of BNP have been used in the diagnosis of CHF. BNP levels have been found to increase in proportion to the degree of left ventricular dysfunction and the severity of CHF symptoms and monitoring the levels of circulating BNP has been used to monitor the effectiveness of therapy. Significant decreases in BNP levels correlate with a longer interval between admissions. Thus, BNP monitoring allows therapy to be tailored to maximize the desired effects in an individual patient. Levels of BNP precursor molecules such as the N-terminal proBNP (NT-proBNP), which is released when BNP is cleaved from its precursor, a 108 amino acid molecule, referred to as "pre pro BNP) have also been measured in assays to diagnose CHF, particularly when the patient's therapy includes being treated which a synthetic BNP molecule.

The inability to determine when a patient's CHF is worsening (before a patient gains several pounds in weight and/or edema is greatly increased) until the patient has a doctor's appointment or requires hospitalization will result in a delay of treatment. While in vitro diagnostic assays measuring BNP levels are now in use, these assessments are point-in-time assessments that do not provide the clinician a complete profile of a patient's changing status. Moreover, required changes to the patient's therapy will be delayed.

A recent development in in vitro assays is the use of biosensors as a substrate for the assay. Biosensors are electronic devices that produce electronic signals as the result of biological interactions. Biosensors are commonly divided into two groups. Catalytic sensors that use enzymes, microorganisms, or whole cells to catalyze a biological interaction with a target substance. Affinity systems use antibodies, receptors, nucleic acids, or other members of a binding pair to bind with a target substance, which is typically the other member of the binding pair. Biosensors may be used with a blood sample to determine the presence of an analyte of interest without the need for sample preparation and/or separation steps typically required for the automated immunoassay systems.

Implantable electrochemical biosensors have recently become an important tool for analyzing and quantifying the chemical composition of a patient's blood. For example, glucose sensors are generally employed to measure blood glucose levels in patients having diabetes. Such biosensors are described in U.S. Published Application No. 2002/0120186, the teachings of which are incorporated herein by reference.

It would be desirable to have implantable biosensors for use in in vivo detection and monitoring of biologically relevant markers in the diagnosis and treatment of cardiovascular diseases, including heart failure and myocardial infarction.

SUMMARY OF THE INVENTION

The present invention provides an implantable sensor system for detecting and/or monitoring the presence and concentration of a desired analyte in a patient. In one embodiment of the invention, the system includes a biochemical sensor to detect levels of a desired cardiac marker or markers such as BNP in the intra-cardiac circulatory system or cardiac tissue, a controller and processor to measure the levels of the cardiac marker and optionally to store the data, and an external user-interface system to display the data. In one embodiment, the system further includes circuitry to trigger a patient alert if the level of the measured cardiac marker exceeds a predetermined critical level.

The sensor system of the invention may be deployed on an intra-cardiac lead or other delivery device as a stand-alone system or incorporated into an implantable medical device such as a pacemaker, defibrillator or cardiac resynchronization therapy (CRT) system. When incorporated into an implantable medical device, the sensor may also be used in cooperation with the device in the therapeutic treatment provided by the device. In some embodiments, the sensor system is deployed on an intra-cardiac lead placed in the coronary sinus orifice of the right atrium of the heart.

In one embodiment of the invention, the sensor is a nanoscale device. The sensor system includes a biological recognition element attached to a nanowire and a detector able to determine a property associated with the nanowire. The biological recognition element is one member of a binding pair where the cardiac marker or analyte being measured is the other member of the binding pair. Preferably, the nanowire sensor includes a semiconductor nanowire with an exterior surface formed thereon to form a gate electrode and a first end in electrical contact with a conductor to form a source electrode and a second end in contact with a conductor to form a drain electrode. In one aspect of the invention the sensor is a field effect transistor comprising a substrate formed of an insulating material, a source electrode, a drain electrode and a semiconductor nanowire disposed there between with a biological recognition element attached on a surface of the nanowire. When a binding event occurs between the biological recognition element and its specific binding partner a detectable change is caused in a current-voltage characteristic of the field effect transistor.

In one embodiment the sensor system includes an array of sensors. One or more of the sensors in the array is associated with a protective member that prevents the associated sensor from interacting with the surrounding environment. At a selected time, the protective member may be disabled, thereby allowing the sensor to begin operating to interact with the surrounding fluid or tissue so that the biological recognition element can interact with the other member of its binding pair if that pair member is present.

In another aspect of the invention, the protective member is formed of a conductive material that can oxidize, is biocompatible, bio-absorbable, and that may be dissolved in solution such as blood upon application of an electric potential. For example, a sensor may be formed within a well of a substrate that is capped by a conductive material such as a biocompatible metal or an electrically-erodible polymer. In another embodiment, the protective member is formed using a material that dissolves over a predetermined period of time.

At a given time, one or more activated sensors from the sensor array may be utilized to determine levels of desired analytes by detecting a detectable signal generated when a substance binds to a biological recognition element of the sensor. The data is then processed and compared to stored data to provide a more accurate indication of a biological or other condition. Another processing scheme may be utilized to obtain a measurement that may then be used to monitor a patient's condition, or modify therapy delivery.

In one embodiment, the sensor system includes a therapy delivery system for providing therapy based on the levels of one or more of the cardiac markers being measured. The therapy delivery system may include a drug pump, a circuit to provide electrical stimulation to tissue, or any other type of therapy delivery means known in the art.

DETAILED DESCRIPTION OF THE INVENTION

Figure 1:
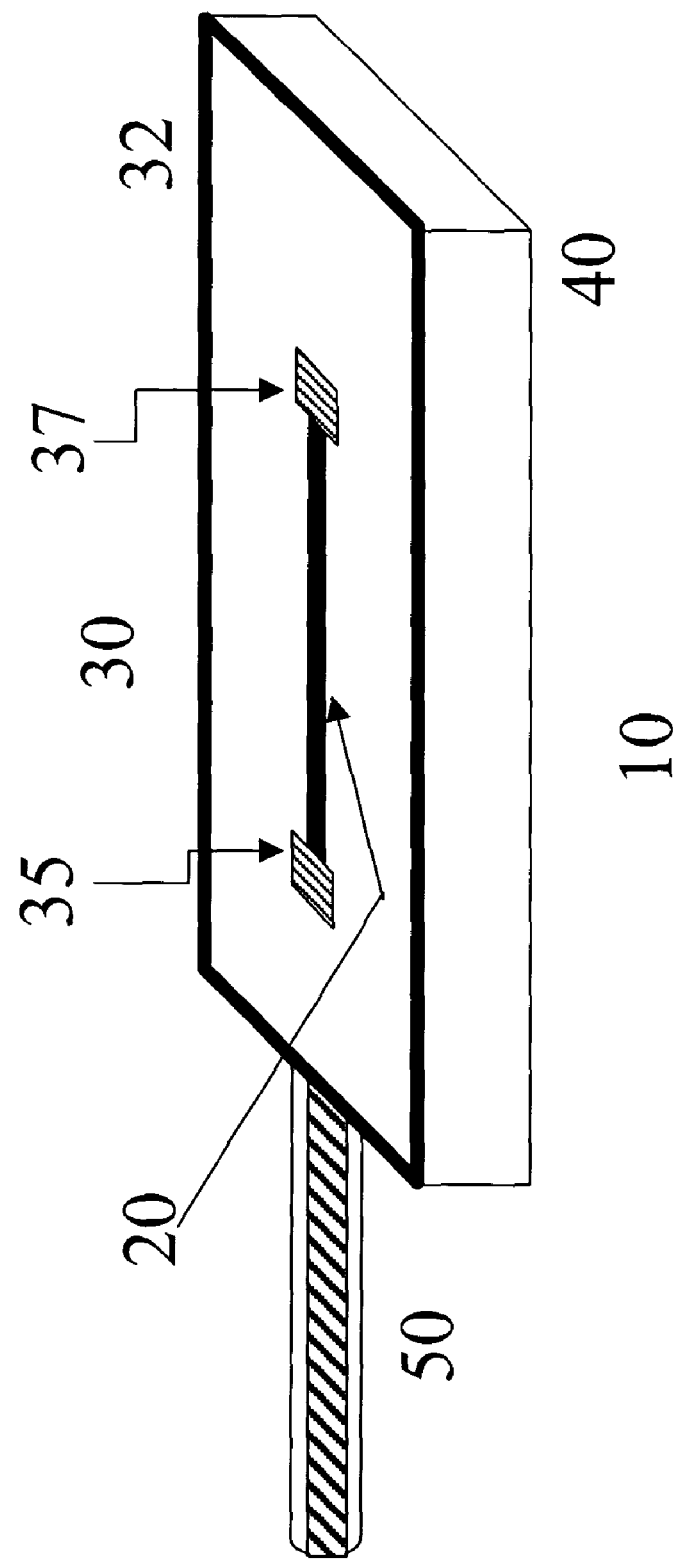
FIG. 1 is a diagram illustrating one embodiment of a sensor according to the current invention.

The present invention relates to an implantable affinity biosensor system for continuous in vivo monitoring of levels of analytes, such as cardiac markers, as a stand-alone system or as part of an implanted or implantable medical device ("IMD"), such as a pacemaker, defibrillator, CRT system and the like. Preferably, the biosensor includes a nanowire field effect transistor substrate having a biological recognition element attached thereto capable of binding to a cardiac marker of interest.

A "nanowire" as used herein refers to an elongated nanoscale semiconductor that, at any point along its length, has at least on cross-sectional dimension and, in some embodiments, two orthogonal cross-sectional dimensions less than 1,000 nanometers. In some embodiments the nanowire has at least one cross-sectional dimension ranging from about 0.5 nanometers to about 200 nanometers. In one embodiment, the nanowire refers to an overlayer row resulting from the deposition of a metal on a silicon surface. Such a nanowire desirably has a width of about 1 to 4 nm and a length of 10 nm or longer.

Nanowires useful in the sensor system of the invention includes any nanowires, including carbon nanowires, organic and inorganic conductive and semiconducting polymers. Other conductive or semiconducting elements of various nanoscopic-scale dimensions can be used in some instances. U.S. Published Application No. 2002/0117659, the teachings of which are herein incorporated by reference, describes nanowires and nanotubes that may be used with the invention.

A primary criteria for selection of nanowires and other conductors or semiconductors for use in the invention is whether the nanowire itself is able to non-specifically bind a substance in the area where the sensor system will be implanted and whether the appropriate biological recognition element, i.e. specific binding pair member, can be attached to the surface of the nanowire.

The nanowire used in the sensor system is desirably an individual nanowire. As used herein, "individual nanowires" means a nanowire free of contact with another nanowire (but not excluding contact of a type that may be desired between individual nanowires in a crossbar array). Generally, each sensor element of the invention will include an individual nanowires. When multiple sensor elements are located or arranged together in one housing, for example in an array, a row or column of individual nanowire sensor elements may be associated together that each specifically bind the same analyte so that they provide a nanowire sensor element set. In one embodiment, each individual nanowire sensor element within a sensor element set will be activated simultaneously and the detectable signal produced by each individual sensor will be detected simultaneously. Methods of making individual nanowires is known.

The biological recognition element refers to any agent that is capable of binding to a cardiac marker of interest. Preferably, the element is a binding pair member that binds to a desired analyte with specificity, i.e., has a higher binding affinity and/or specificity to the analyte than to any other moiety. Such binding pairs are well known and include the following: antigen-antibody, growth factor-receptor, nucleic acid-nucleic acid binding protein, complementary pairs of nucleic acids and the like. Preferably, the biological recognition element is an antibody or an effective portion thereof retaining specific binding activity for the analyte. Effective portions include, for example Fv, scFv, Fab, $Fab_2$ and heavy chain variable regions or a chimeric molecule or recombinant molecule or an engineered protein comprising any of the portions.

The biological recognition element is attached to the nanowire. As used herein, "attached to," encompasses all mechanisms for binding antibodies and proteins, directly or indirectly to surfaces so that when the sensor is implanted and the biological recognition element interacts with its surrounding environment the element remains associated with the surface. Such mechanisms chemical or biochemical linkage via covalent attachment, attachment via specific biological binding (e.g., biotin/streptavidin), coordinative bonding such as chelate/metal binding, or the like.

Illustrative embodiments of the invention are shown in the Figures. As will be readily apparent to those skilled in the art upon a complete reading of the present application, the present methods and systems are applicable to a variety of systems other than the embodiments illustrated herein.

FIG. 1 shows one example of an implantable affinity nanosensor of the invention. The sensor system 10 includes a single nanowire 20 positioned above upper surface 32 of the substrate 30. A housing 40 that may be a hermetic sensor integrated circuit package. The sensor system also includes electrodes 35 and 37, respectively, that are connected with electrical connections, which in this embodiment are located in the housing. The sensor system is deployed on a lead 50 that may be connected to a user interface and/or to an IMD.

The substrate 30 is typically made of a polymer, silicon, quartz or glass. The electronic circuitry may be powered by one or more batteries, or alternatively, may receive power via implanted medical electrical leads coupled to another implantable medical device (IMD) as will be described below. Any electronic circuitry adapted to provide long-term continuous monitoring may be used in conjunction with the device of the present invention. In some embodiments, the electronic circuitry may be powered by external means.

The housing of the sensor systems of the present invention may use a packaging technique that protects the components of the system in aqueous media. For example, the top and bottom portions of the housing may be manufactured from a thermoformed high-density polyethylene. The area inside the housing surrounding the electronic circuitry and other components may be filled with a material that cushions the system while not interfering with circuit operation. The filling material may be a mixture of petroleum wax and low melting temperature resins, for instance.

Figure 2:
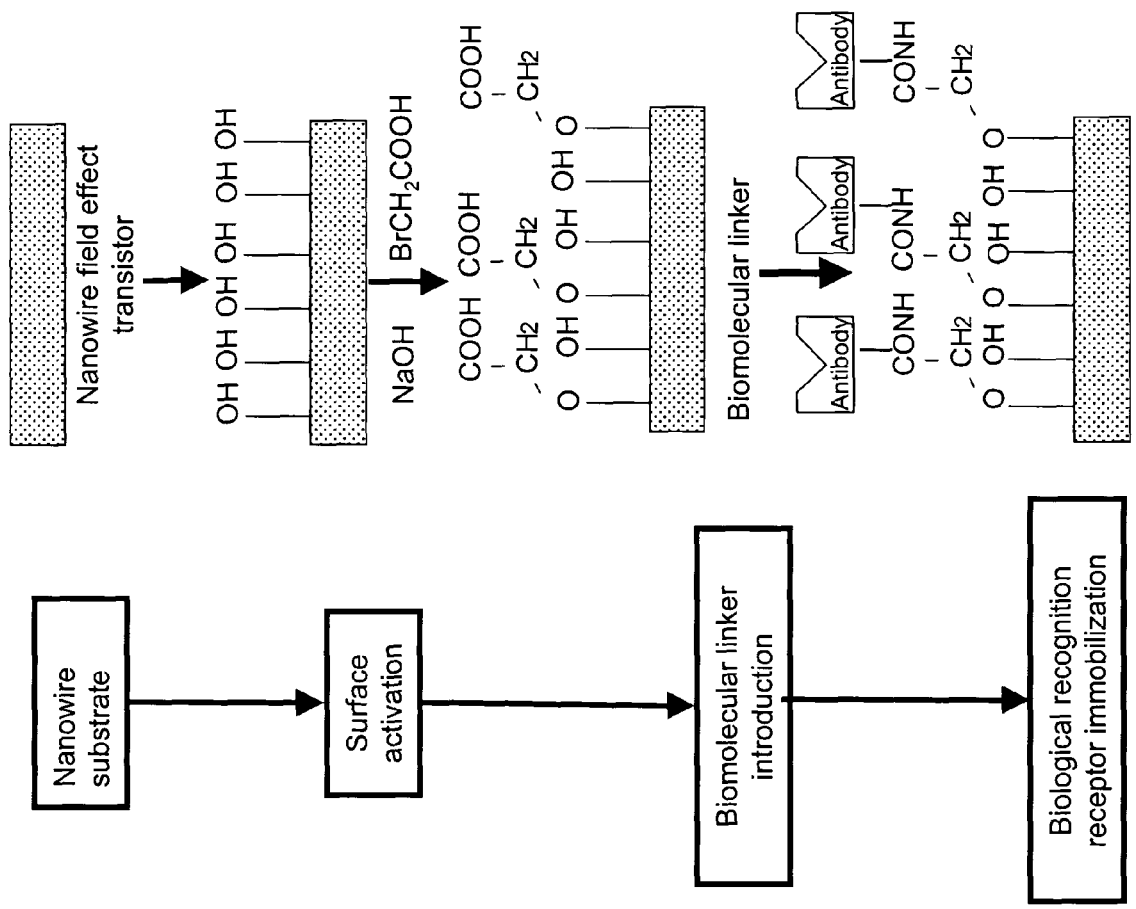
FIG. 2 is a flow chart illustrating one method of attaching a biological recognition element to a sensor such as that shown in FIG. 1.

FIG. 2 is a schematic illustrating the steps for attaching the biological recognition element to the surface of a nanowire sensor 10 such as that shown in FIG. 1. The surface of the nanowire is chemically activated as shown and a biomolecular linker chosen to bind the antibody of interest is added and allowed to react with the chemically activated surface to facilitate binding of antibody or other biological recognition element to the surface.

The method of attaching the biological recognition element will differ depending on the material of nanosensor surface and the binding pair used. When the element is an antibody or protein may be performed by covalently bonding the protein to the surface with bi-functional molecules such as glutaraldehyde, carbodiimides, biotin-avidin, and other molecules with one or more functional groups on each of at least two ends as are well known to those skilled in the art. Additionally, bi-functional spacer molecules such as N-hydroxysuccinimide derivatized polyethylene glycols may be used to bind the protein.

Figure 3:
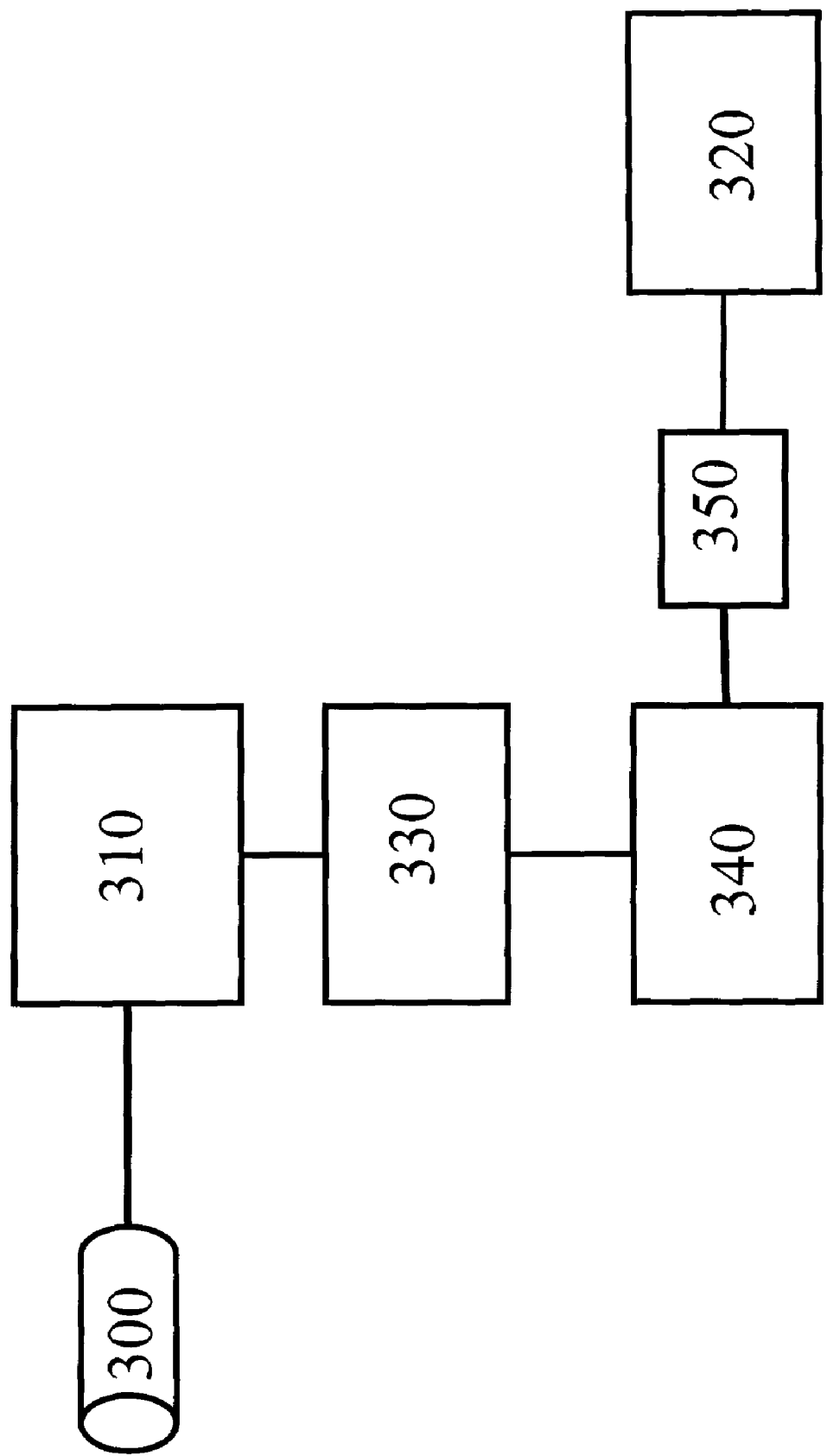
FIG. 3 is a diagram illustrating one embodiment of a sensor system according to the current invention.

FIG. 3 is a block diagram showing an example of a nanosensor system of the invention. The affinity nanowire sensor 300 such as that shown is FIG. 1 is carried on a medical lead for implantation in a patient. Desirably, the sensor is located in cardiac tissue or in the intra-cardiac circulatory system of the patient or elsewhere in the blood stream where levels of certain cardiac markers associated with cardiovascular diseases may be measured. In one aspect of the invention, the cardiac markers being detected include without limitation, BNP, pre proBNP, NT pro BNP, C-type reactive protein, Troponin I and T, respectively, Myoglobin, D-Dimer, cytokines, such as tissue necrosis factor alpha, and other cardiac markers known in the art. Sensor 300 is connected to a detector 310 that will measure the detectable signal generated by the sensor when one or more molecules of the cardiac marker or markers being measure binds to the biological recognition element attached to the nanowire, where the amount of signal generated can be used to determine the level of the cardiac marker present in the patient. The detector may be associated with a user interface display 320 that may be accessed by the patient and/or the patient's health care provider either as a continuous display or stored in a processor (shown as 520 in FIG. 5). In one embodiment, the detector 310 can be connected to a telemeter 330 that will transmit the sensed information to receiver 340 that may be associated with a server 350. The server 350 may include a patient database with other patient information that may be relevant to monitoring the patient's status. In the system of FIG. 3, the server 350 is optionally accessible through an internet access management system 320 so that the health care provider can access information obtained from the continuous monitoring of the levels of one or more of the patient's cardiac markers.

Figure 4:
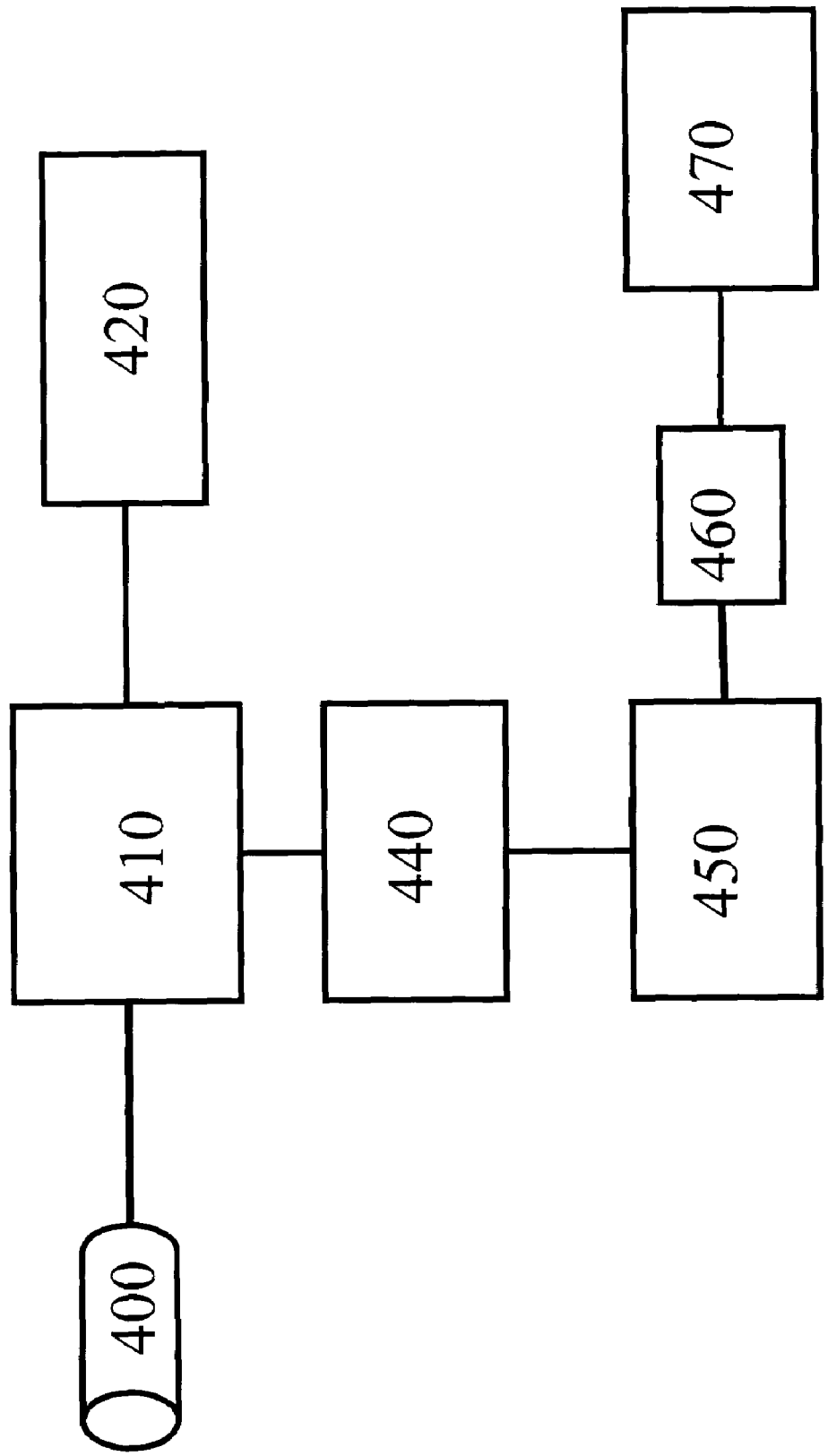
FIG. 4 is a diagram illustrating one embodiment of a sensor system according to the current invention including a therapy delivery system.

FIG. 4 shows a block diagram of a nanosensor system of the invention associated with an implanted medical device (IMD) and optionally with an electrical stimulation system of the IMD. In this embodiment, a nanosensor 400 such as that described in FIG. 1 is connected with a detector 410, which may also include an electrical stimulator, and to electrical stimulation leads 420 associated with an IMD, including without limitation, a CRT, pacemaker, or defibrillator. Detectable signal produced by the nanosensor 400, the amount of which is related, directly or indirectly, to the levels of one or more cardiac markers in the patient are received by the detector and/or stimulator and the levels of desired cardiac markers determined. The information may be processed by a controller (shown as 500 in FIG. 5) within the detector to vary parameters of the IMD in response to changes in the levels of the measure cardiac marker in the blood or tissue of the patient. A telemeter 440 may be included that is associated with the detector 410 to transmit information received by detector to a receiver 430. The receiver 430 is in one embodiment connected to a server 450 that provides for internet access to patient information through a user interface 460 by the health care provider or patient.

Figure 5:
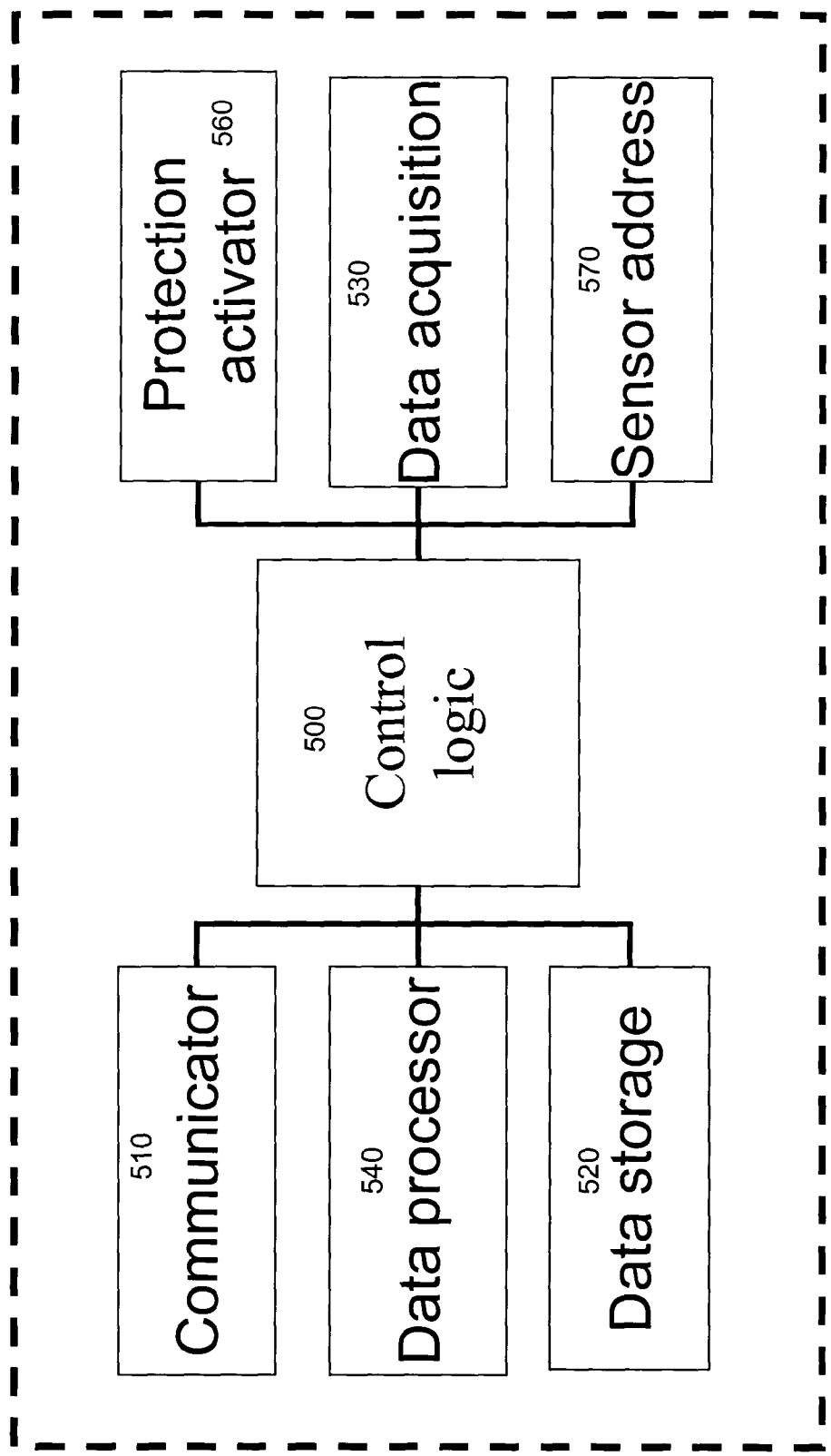
FIG. 5 is a system block diagram of one embodiment of a controller that may be used with the sensor system of the invention.

FIG. 5 is a system block diagram of one embodiment of a controller of a nanosensor system of the invention. The controller 500 may be provided within any IMD known in the art, or may be part of the detector or processor elements of the nanosensor systems, such as the systems shown in FIGS. 3 and 4. The controller 500 may include circuitry for delivering electrical stimulation for pacing, cardioversion, and/or defibrillation purposes on electrical stimulation outputs.

The controller 500 may include a communicator 510, such as a telemetry system described in commonly-assigned U.S. Pat. No. 6,169,925, incorporated herein by reference in its entirety. The use of this telemetry system would provide a system capable of long-range communication with personal patient communication devices. Such patient communication devices may have an alarm function to alert the patient of sensor readings outside a range considered acceptable. The alarm may also be included to inform the user of actions that should be taken by the user in response to an original alert. The level of urgency of the alarm could also be encoded into the signal changes. The alarm may be of any type of patient alert known in the art, including without limitation, an audible alarm, a visual alarm, or an alarm that alerts the patient through vibration. Additionally, the patient could be informed of information through muscle or nerve stimulation from additional electrodes on the device. In another embodiment, a telemetry signal may be provided to an external device to deliver an automatic alert in the event an emergency situation is detected. For example, if levels of cardiac markers indicated that a patient was suffering a heart attack, emergency workers may be automatically contacted via an uplink to a communications system. Patient data may automatically be provided to emergency health-care workers using information stored with the data storage element 520. The controller 500 may also include a data acquisition element 530 and a data processor 540.

In one embodiment of the invention, the nanosensor of the invention may include a protective member located adjacent the sensor to shield the sensor from a surrounding environment for a selectable time period. The controller 500 may include a protection activator element 560 that would generate a signal that would result in the protective member or a predetermined portion of the protective member(s) to be oxidized, dissolved or otherwise removed so that the nanosensor is allowed to become operational. When a plurality of sensor elements are used, one or more protective members can be associated with one or more sensor elements, where the selectable time period differs. In one embodiment, one or more protective members may be associated with one set of nanowire sensor elements so such protective members may be disabled simultaneously to simultaneously activate the individual nanowire sensor elements within the set. In another embodiment, one or more protective members may be associated with a first set of nanowire sensor elements, wherein one or more first protective member(s) will shield the set of sensor elements for a first selectable time period and a second one or more protective members will shield a second set of nanowire sensor elements for a second selectable time period. The first set of sensor elements may be activated to measure levels of an analyte at the first time, and the second set of sensor elements may be activated at a second time and levels of analyte measured. In yet another embodiment, first and second sets of nanowire sensor elements may include first and second biological recognition elements that specifically bind different substances. In this embodiment, one protective member may be associated with both sets of nanowire sensor elements and when that protective member is disabled both sets of sensor elements are activated so that the level of more than one analyte may be determined simultaneously. Alternatively, one or more protective members may be associated with each set of sensor elements and the protective members disabled sequentially. A person of ordinary skill in the art will know how to optimize the activation of individual nanowire sensor elements in desired numbers in a set to obtain a desired sensitivity and specificity of analyte being measured. In one of the preferred embodiments, the number of individual nanowire sensor elements in a set will be chosen to provide nanogram to picogram sensitivity.

The processor may be a microprocessor or other processing circuit as is known in the art. Storage device may comprise Random Access Memory (RAM), Read-Only Memory, registers, a combination thereof, or any other type of memory storage device suitable for use in implantable medical devises. The controller 500 may also include a sensor address 570.

The controller 500 may additionally include a protection activator that will cause a protective member that may be formed over the sensor in one embodiment to prevent the sensor from being exposed to bodily fluids prior to a selected time to dissolve.

Protective members are described for use with sensors in commonly assigned U.S. Published Patent Application No. 2002/0120186, the teachings of which are herein incorporated by reference. In one embodiment, the protective member consists of a thin film of conductive material. Any conductive material that can oxidize, is biocompatible, bio-absorbable, and that may be dissolved in solution such as blood upon application of an electric potential can be used for the fabrication of a protective member. Examples of such materials include copper, gold, silver, and zinc, and some polymers.

Protective members may be formed by injection or spin coating. In one embodiment, the nanosensor is positioned with a well formed in the substrate. The protective member may be sized to cover the well or may extend beyond the edge of the well to partially cover the substrate. In one embodiment the well can be capped with the protective member by capillary action, by drawing the material partially into the well with a vacuum or other pressure gradient, by melting the material in to the well, by centrifugation and related processes, by inserting solids into the well, or by any combination of these or similar methods.

In one aspect, the protective member is electrically and mechanically coupled to a respective conductor referred to as the anode. An additional "cathode" conductor is desirably located adjacent to, but electrically and mechanically isolated from, a respective reservoir. A voltage difference applied across the anode and cathode when the protective member is placed in a conductive solution causes electrons to pass from the anode conductor to the cathode conductor through the conductive solution. This, in turn, causes the protective member, which may be considered the anode of the circuit, to oxidize and dissolve into the surrounding fluids, exposing the sensor to surrounding body fluids so that the sensor becomes operational and the biological recognition element may interact with the surrounding environment.

Although the foregoing examples described protective members that dissolve or erode through the use of a current, any bio-absorbable material that will dissolve within a patient's body in a predictable time period may be used. For example, in an embodiment of the invention where more than one sensor element is included in the system, one or more of the sensor elements may be left unprotected, while one or more additional sensor elements may be associated with a respective protective member that substantially absorbs over a first time period. Yet another set of sensor elements may each be associated with protective members formed of another material known to substantially dissolve over a second time period which is longer than the first time period, and so on. Use of protective members with a plurality of sensor elements to provide for sequential activation of one or more sensor elements can increase the functional life of the sensor by reducing the time period the biological recognition period is exposed to the surrounding environment and reducing the likelihood of non-specific binding of proteins and other materials present in the body to the sensor element in a way that will interfere with the specific binding of analyte or a substance related to the level of analyte present in the patient. In some embodiments, protective members may be used with a plurality of sensor elements to provide for activation of a desired number of sensor elements necessary to control the gain or signal to noise of the sensor elements. For example, in order to obtain a meaningful measurement of levels of an analyte of interest in a patient, it may be necessary to activate more than one sensor element to increase the level of detectable signal being produced.

Figure 6:
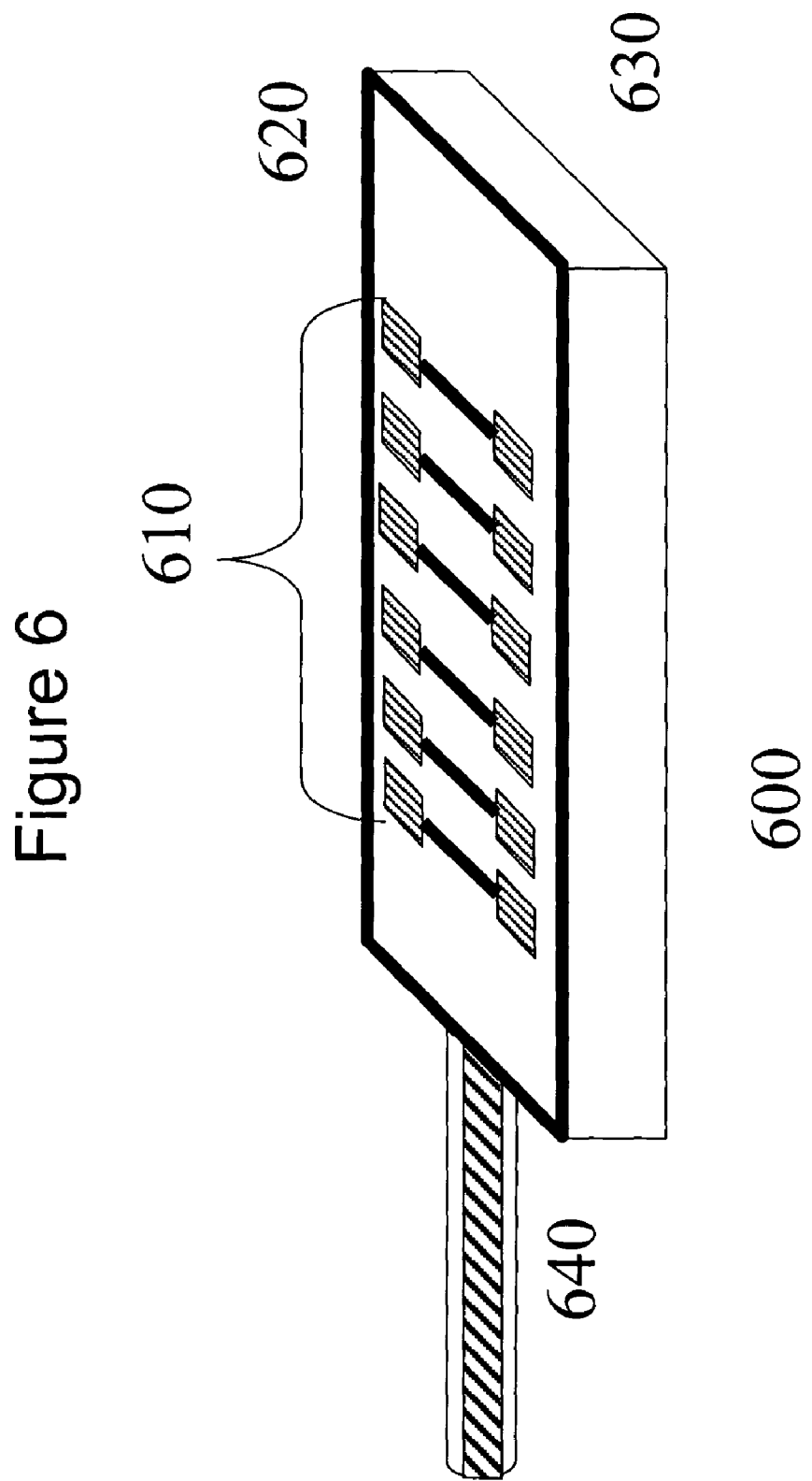
FIG. 6 is a diagram illustrating an embodiment of a sensor of the invention.

FIG. 6 is a diagram illustrating an example of an implantable nanosensor array 600 for monitoring of multiple analytes. A plurality of nanowire field effect transistors 610 are positioned on substrate 620. Substrate 620 is positioned over a hermetic sensor integrated circuit package 630, which includes electronic circuitry of the sensor. The sensor is arranged on or connected to lead 640. Although six nanosensors are shown, any other number of nanosensors as may be supported by substrate 620 is possible.

Figure 7:
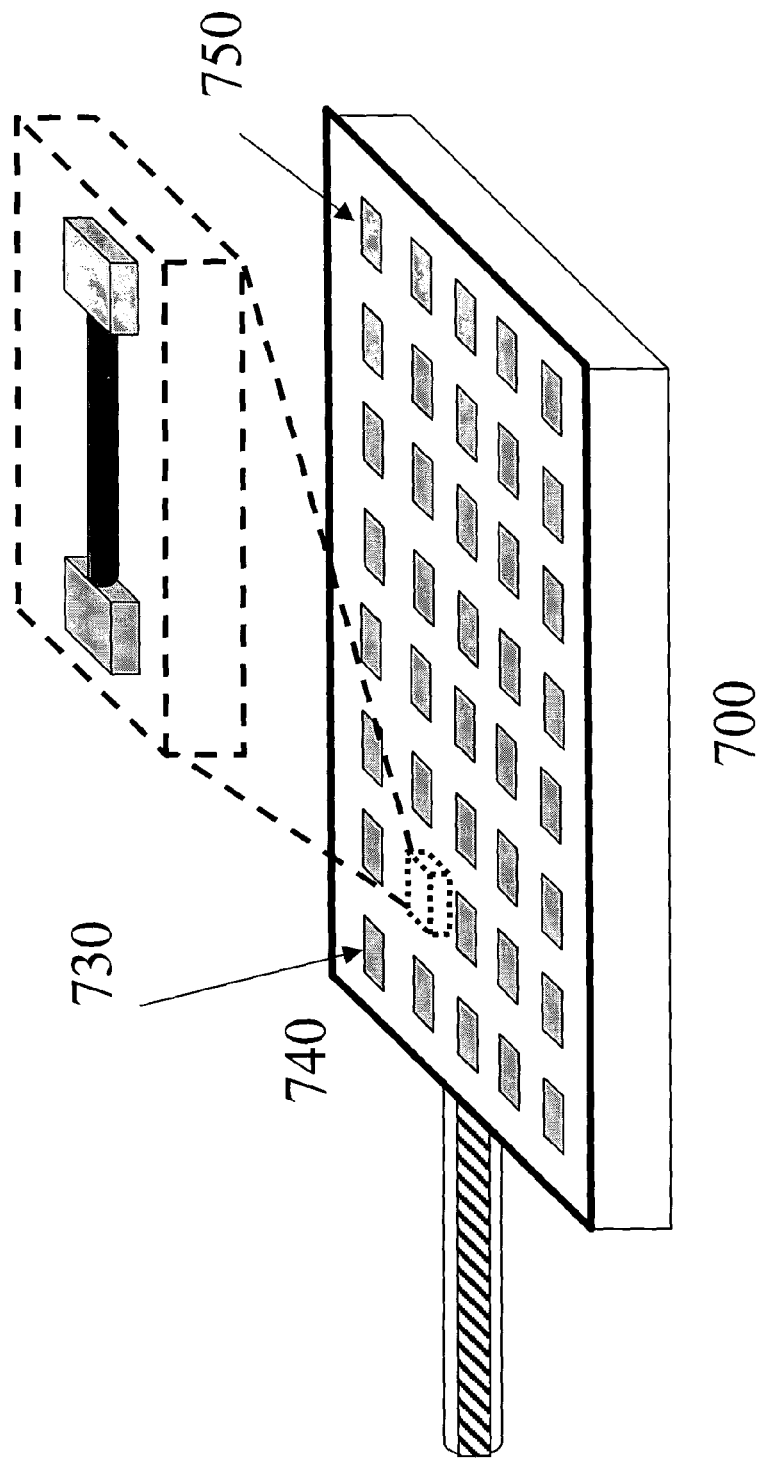
FIG. 7 is a diagram illustrating one embodiment of a sensor of the invention having a protective member and a plurality of individual nanowire sensor elements.

FIG. 7 is a diagram illustrating an example of an implantable nanosensor array 700 for monitoring of multiple analytes or for monitoring of a single analyte over a selected period of time or a combination thereof. The array shown in FIG. 7 includes a plurality of individual nanosensors 720, each positioned within a well 740 formed in the substrate 750 and covered with protective member 730. In one embodiment, each nanosensor includes a biological recognition element for the same cardiac marker. In use, the array may be implanted within a patient and a predetermined number of nanosensors rendered operational by dissolving the corresponding protective member. The number of nanosensors rendered operational will be determined by the specificity and sensitivity of the binding between the biological recognition element and the cardiac marker of interest and how the detectable signal data is processed. If, under certain conditions, the levels of cardiac marker of interest increase significantly, the specific binding of cardiac marker to the biological recognition element in one nanosensor may not be sufficient to accurately measure the change.

In another embodiment, each nanosensor must be activated prior to use by applying signals on associated control and address lines to remove a protective member adjacent to the nanosensor in a manner discussed above. Prior to activation, a nanosensor is not exposed to the surrounding environment, so degradation does not occur. After the protective member is removed, sensing may be performed with the sensor until such a time as the sensor performance is determined to be degrading and outside a pre-defined range of accuracy. Thereafter, the nanosensor may be left unused and a different nanosensor activated in its place. In this manner, the implanted sensor system may be used for long periods without requiring replacement.

Figure 8:
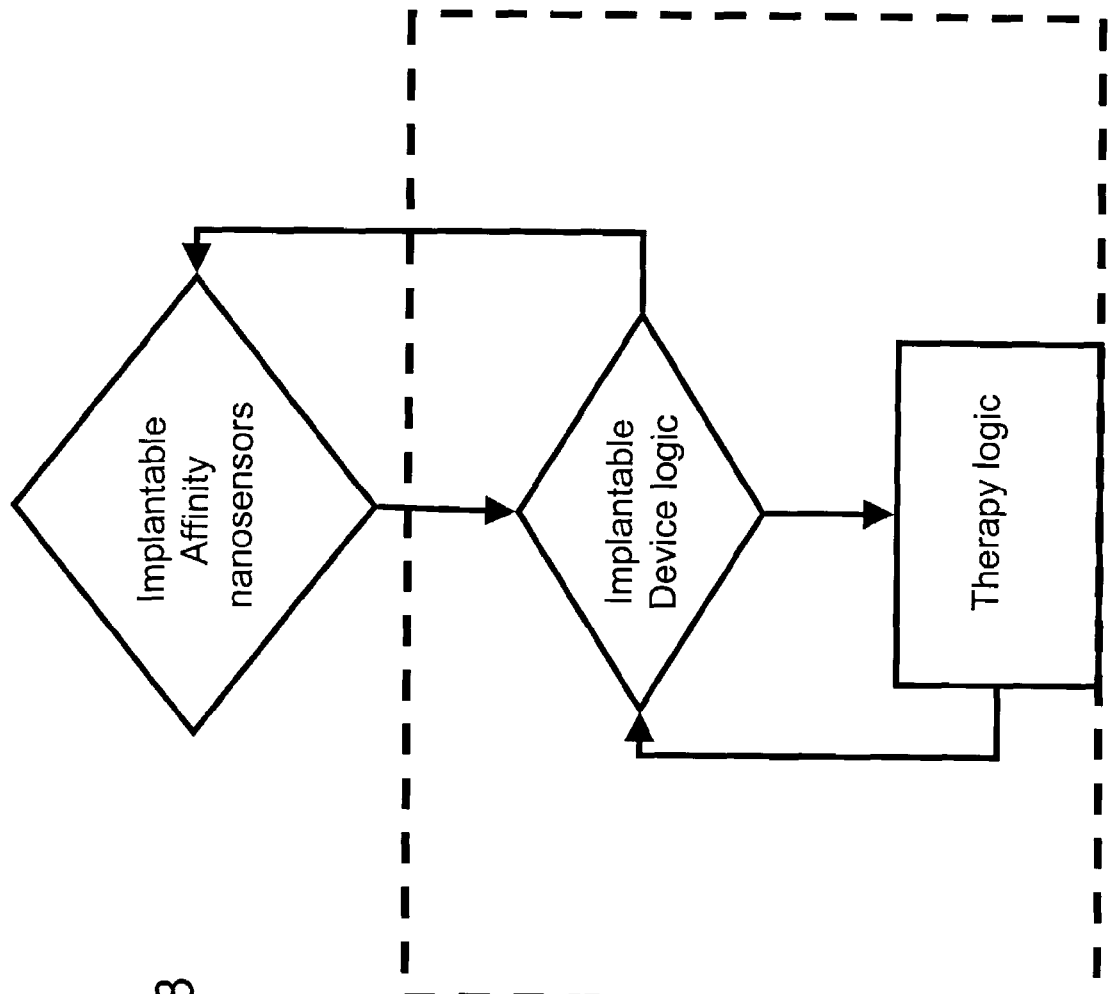
FIG. 8 is a flow chart illustrating one embodiment of a method as may be practiced with the current invention.

FIG. 8 is a flowchart illustrating an example of a closed-loop nanosensor system that works in conjunction with therapy delivered by and IMD. The type of therapy may involve pacing, defibrillation, drug delivery, monitoring and/or patient management therapies. In the embodiment exemplified in FIG. 8, the therapy is provided by an IMD such as a pacemaker, defibrillator or the like. Computer implemented software logic system in the nanosensor system and/or in the implantable device activates one or more nanosensors in implanted in a patient and begins to measure the levels of a desired cardiac marker in the patient. When the nanosensor determines that the levels of the cardiac marker or markers being measured have increased or decreased to a level that indicates that the patient's status is worsening, the therapy parameters of the IMD may be adjusted accordingly. The nanosensor continues to measure the levels of cardiac marker of interest and appropriate adjustments made in the therapy.

When the IMD is a CRT system, an increase in levels of a cardiac marker such as BNP may be used to optimize AV and VV timing, to assess the impact of a therapeutic regime on reverse remodeling of the heart or to assess the impact of concomitant drug therapy. Operating under software and/or hardware control, a processing circuit processes the received signal(s) to determine a course of action. Alternatively, the processor may average one or more nanosensor readings, or may use a voting scheme to discard out-of-range signals or may correlate the levels of more than cardiac marker prior to determining the course of action.

The nanosensor system of the invention is particularly useful in monitoring levels of cardiac markers in patients with cardiovascular diseases and particularly in monitoring levels of BNP in such patients. Methods for determining the prognosis of a patient diagnosed with heart failure or other cardiovascular diseases are described in U.S. Published Patent Application No. 2003/0022235. Briefly, the method includes identifying a BNP level, or the level of a marker related to BNP and associated with an increase in symptoms associated with the patient's cardiovascular disease. Once that level has been determined, a nanosensor system of the invention having a biological recognition element that is a binding pair member of BNP or related marker attached to a nanowire field effect transistor is be implanted in the patient's intra-cardiac circulatory system, either as a stand-alone device or as part of an implantable medical device already implanted in the patient or to be implanted in the patient. The nanosensor controller will measure the patient's BNP levels at predetermined intervals, store the measurements and compare them to the prognostic level of BNP previously determined for the patient. If the BNP level indicates that the patient's condition is worsening, then a patient alert will be triggered so that the patient knows to contact his or her health care provider. Optionally, if the BNP level indicates that the patient's condition is worsening the parameters of the therapy may be automatically be adjusted to a more optimal setting.

Preferably the biological recognition element is an antibody or a fragment thereof that specifically binds to peptide epitopes within the BNP molecule. In one embodiment the antibody is a monoclonal antibody. Antibodies and other elements that will specifically bind to BNP or markers related to BNP are known. For example, U.S. Pat. No. 6,124,430 describes antibodies that bind to epitopes within the hBNP molecule, the teachings of which are incorporated herein by reference.

In another embodiment of the invention, a nanosensor system of the invention that includes an array of individual nanosensors adapted to measure the levels of more than one cardiac marker may be used in a method for diagnosing organ failure. Preferably, the cardiac markers of interest include markers that indicated a pressure, volume change and stress to the heart (e.g. BNP and pro-BNP) and markers that are indicative of tissue damage (e.g. cardiac Troponin I). Methods of correlating the measurements of such marker levels obtained using in vitro diagnostic assays to the diagnosis of heart failure are described in U.S. Pat. No. 6,461,828, the teachings of which are herein incorporated by reference.

All patents and publications referenced herein are hereby incorporated by reference in their entireties. It will be understood that certain of the above-described structures, functions and operations of the above-described preferred embodiments are not necessary to practice the present invention and are included in the description simply for completeness of an exemplary embodiment or embodiments. In addition, it will be understood that specifically structures, functions and operations set forth in the above-referenced patents can be practiced in conjunction with the present invention, but they are not essential to its practice. It is therefore to be understood that within the scope of the appended claims, the invention may be practiced otherwise than as specifically described without actually departing from the spirit and scope of the present invention.

What is claimed is:

1. An implantable sensor system for determining the presence or amount of an analyte in a patient, comprising:
   a. a sensor element comprising a biological recognition element associated with a portion or portions of a transducer, the biological recognition element being capable of specifically binding to a substance in the patient in an amount related to the presence or amount of the substance, wherein the substance is BNP or a marker related to BNP, and wherein when the substance is bound to the biological recognition element a detectable signal is produced; and b. a controller associated with the sensor element to measure the detectable signal and relate the amount of the detectable signal measured with the presence or amount of the substance present in the patient;

wherein the sensor element is adapted to be implanted within the intracardiac circulatory system of the patient's heart and wherein the controller is adapted to compare measured levels of the substance to preselected levels stored in the controller and the controller includes a circuit to vary the AV interval of a cardiac resynchronization therapy device in response to measured levels of the substance.

2. The implantable sensor system of claim 1, wherein the marker related to BNP is pre proBNP or NT pro BNP.

3. The implantable sensor system of claim 1, wherein the biological recognition element is mounted on a nanowire.

4. The implantable sensor system of claim 3, wherein the nanowire comprises a gated nanowire field effect transistor.

5. The implantable sensor system of claim 1, further including a control circuit coupled to the protective member to disable the protective member after the selectable time period.

6. The implantable sensor system of claim 1, wherein the biological recognition element is an antibody or portion of an antibody capable of binding to the analyte.

7. The implantable sensor system of claim 1, wherein the biological recognition element is capable of reversibly binding to the substance.

8. An implantable cardiac resynchronization therapy system, comprising:

a sensor element comprising a biological recognition element associated with a portion or portions of a transducer, the biological recognition element being capable of specifically binding to a substance in the patient in an amount related to the presence or amount of the substance, wherein the substance is BNP or a marker related to BNP, and wherein when the substance is bound to the biological recognition element a detectable signal is produced; and a cardiac resynchronization therapy device comprising a controller associated with the sensor element to measure the detectable signal and relate the amount of the detectable signal measured with the presence or amount of substance present in the patient, the controller (i) being adapted to compare measured levels of the substance to preselected levels stored in the controller and (ii) including a circuit to vary the AV interval of the cardiac resynchronization therapy device in response to measured levels of the substance.

9. The system of claim 8, further comprising an intracardiac lead connectable to the cardiac resynchronization therapy device, wherein the sensor element is deployed on the lead.

10. The implantable sensor system of claim 8, further comprising a protective member located adjacent the sensor element to shield the biological recognition member from a surrounding environment for a selectable time period.

11. The implantable sensor system of claim 8, wherein the marker related to BNP is pre proBNP or NT pro BNP.

12. The implantable sensor system of claim 8, wherein the biological recognition element is mounted on a nanowire.

13. The implantable sensor system of claim 12, wherein the nanowire comprises a gated nanowire field effect transistor.

14. The implantable sensor system of claim 8, further including a control circuit coupled to the protective member to disable the protective member after the selectable time period.

15. The implantable sensor system of claim 8, wherein the biological recognition element is an antibody or portion of an antibody capable of binding to the analyte.

16. The implantable sensor system of claim 8, wherein the biological recognition element is capable of reversibly binding to the substance.

17. An implantable cardiac therapy system,
comprising:
a BNP sensor producing an output signal indicative of BNP level;
a cardiac therapy device providing ventricular pacing on expiration of AV intervals, comprising a memory for storing sensed levels of BNP and a controller including a circuit to optimize the AV intervals in response to increases in sensed levels of BNP.

18. The system of claim 17, wherein the controller is adapted to compare sensed levels of BNP to preselected levels stored in the controller and the controller includes a circuit to vary the AV intervals of the cardiac therapy device in response to sensed levels of BNP.

19. The system of claim 17, further comprising an intracardiac lead connectable to the cardiac therapy device, wherein the sensor is deployed on the lead.

20. The system of claim 17, further comprising a protective member located adjacent the sensor to shield the sensor from a surrounding environment for a selectable time period.

21. The implantable sensor system of claim 20, further including a control circuit coupled to the protective member to disable the protective member after the selectable time period.

22. The implantable system of claim 17, wherein the sensor is responsive to a marker related to BNP.

23. The implantable system of claim 22, wherein the sensor is responsive to pre proBNP or NT pro BNP.

* * * * *

UNITED STATES PATENT AND TRADEMARK OFFICE
CERTIFICATE OF CORRECTION

PATENT NO.       : 7,632,234 B2                                Page 1 of 1
APPLICATION NO.  : 10/652837
DATED            : December 15, 2009
INVENTOR(S)      : Manda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1109 days.

Signed and Sealed this

Second Day of November, 2010

David J. Kappos
*Director of the United States Patent and Trademark Office*